United States Patent

Kitaoka et al.

[11] Patent Number: 5,983,705
[45] Date of Patent: Nov. 16, 1999

[54] METHOD FOR MEASURING ATMOSPHERIC GAS AND SYSTEM FOR MEASURING ATMOSPHERIC GAS

[75] Inventors: Tatsumi Kitaoka, Yokohama; Toshihiko Matsuura, Kawasaki; Mitsunori Hasegawa, Kawasaki; Shuichi Tanahashi, Kawasaki, all of Japan

[73] Assignees: Fujitsu Limited, Kawasaki, Japan; Software Limited, Yokohama, Japan

[21] Appl. No.: 08/927,814

[22] Filed: Sep. 11, 1997

[30] Foreign Application Priority Data

Sep. 20, 1996 [JP] Japan .................................... 8-250456

[51] Int. Cl.[6] ............................ G01N 9/00; G01N 27/00; G01J 5/02

[52] U.S. Cl. ........................ 73/31.01; 422/98; 250/339.13

[58] Field of Search ................................ 73/31.01, 31.06; 250/339.13; 356/437; 374/128; 422/98

[56] References Cited

U.S. PATENT DOCUMENTS

| 2,899,281 | 8/1959 | Olmer ........................................ 422/96 |
| 3,153,577 | 10/1964 | McCully et al. ......................... 422/98 |
| 3,878,502 | 4/1975 | Rochelle ................................. 367/134 |
| 3,971,630 | 7/1976 | Sandrock et al. ........................ 422/64 |
| 4,271,358 | 6/1981 | Schwarz ............................... 250/338.1 |
| 4,619,821 | 10/1986 | Ely ........................................ 423/578 |
| 5,512,873 | 4/1996 | Saito et al. ........................... 338/22 SD |

*Primary Examiner*—Michael Brock
*Assistant Examiner*—Jay L. Politzer
*Attorney, Agent, or Firm*—Staas & Halsey, LLP

[57] ABSTRACT

A method is disclosed for measuring at least one atmospheric gas in an upper-air region using a plurality of sensors. The step of the method include measuring a temperature of the air using one of a plurality of sensors, which is not affected by gases contained in the air; measuring a temperature of the air using some of the plurality of sensors, each of the sensors being affected by at least one gas contained in the air; and calculating an amount of that atmospheric gas based on measured values obtained from each of the plurality of sensors.

18 Claims, 5 Drawing Sheets

METHOD FOR MEASURING ATMOSPHERIC GAS AND SYSTEM FOR MEASURING ATMOSPHERIC GAS

BACKGROUND OF THE INVENTION

The present invention generally relates to a method for measuring atmospheric gases and a system for measuring atmospheric gases, and particularly, to methods for measuring atmospheric gases and a system for measuring atmospheric gases, by which, information such as an amount and a vertical distribution of gases considered to be responsible for temperature rise on earth, such as atmospheric ozone, carbon dioxide and infrared emission gases, is obtained and the accuracy of a temperature measurement in the conventional upper-air observation of the atmosphere is improved.

Currently, the measurement of a gas, for instance, ozone, contained in the atmosphere is carried out by using the Dobson spectrophotometer, which analyzes ozone by measuring ultraviolet rays from the sun on the earth, or using a ozone sonde which is capable of measuring the vertical distribution of ozone in the atmosphere. A meteorological satellite, by which ultraviolet rays from the sun may be observed, is also employed for measuring ozone.

Observation of carbon dioxide in air is carried out at many places on earth and also in upper-air region using airplanes.

Moreover, there is a method in which a white-painted thermistor sensor sensitive to carbon dioxide, clouds and water vapor but not sensitive to ozone radiation is used.

However, since the above mentioned Dobson spectrophotometer is not small enough to be set in a sonde, it has to be used on the ground, and hence the vertical distribution of ozone cannot be measured.

Also, there are a couple of problems associated with a temperature measurement using an ordinary temperature sensor exposed to air from an airplane or on the ground as follows:

a) since the white-painted thermistor sensor is sensitive to clouds, water, water vapor or carbon dioxide radiation as mentioned above, a large error may occur when there is a significant change in any of the above-mentioned factors;

b) cloud particles may attach to the surface of the sensor and form blackish matter by which the sensor may become sensitive to ozone radiation;

c) when an aluminium-deposited temperature sensor in world-wide use whose surface is coated with a thin layer of SiO is employed, water vapor tends to freeze on the surface and the surface becomes like a "clouded glass". In this state, since the SiO thin layer has a weak absorption in the ozone absorption band in nature, the sensor becomes sensitive to ozone radiation as well. This may cause a large error in the measurements.

If a water repellent is applied on the surface of the above-mentioned sensor in order to avoid this problem, although the freezing of water vapor can be stopped, an error due to the above-mentioned weak absorption in the ozone absorption band of the SiO thin layer still remains. Moreover, since a reflection effect by clouds is relatively increased due to the decreased warming effect by the ozone layer located above, a large error may occur in the measurements, especially in the troposphere.

The above mentioned errors caused by the white-painted thermistor sensor have been recently recognized by an analysis in which the results of measurements obtained when the white-painted thermistor sensor are used and those obtained when a bimetal sensor placed in a protective air flow duct are compared. It is now proposed to set a sensor which has sensitivity to infrared radiation and a senor which is not sensitive to infrared radiation in the same radio sonde and perform measurements of infrared radiation gases in the atmosphere by switching the sensors.

SUMMARY OF THE INVENTION

It is a general object of this invention to provide a method for measuring atmospheric gases and a system for measuring atmospheric gases in which the above mentioned problems are eliminated.

A more specific object of the present invention is to provide methods for measuring atmospheric gas and a system for measuring atmospheric gas, by which information such as an amount and a vertical distribution of gases considered to be responsible for temperature rise or increase on the earth, such as atmospheric ozone, carbon dioxide and infrared emission gases, is obtained.

Another object of the present invention is to provide a method for measuring atmospheric gases and a system for measuring atmospheric gases by which the accuracy of a temperature measurement in the conventional upper-air observation of the atmosphere is improved.

Yet another object of the present invention is to provide a method for measuring atmospheric gases and a system for measuring atmospheric gases by which the destruction of ozone layers in the air or the temperature increase of the earth may be accurately detected.

The objects described above are achieved by a method for measuring at least one atmospheric gas in an upper-air region using a plurality of sensors comprising: measuring a temperature of the air using one of the plurality of sensors, which is unaffected by gases contained in the air, measuring a temperature of the air using some of the plurality of sensors, each of the some of the plurality of sensors being affected by at least one gas contained in the air, and calculating an amount of at least one atmospheric gas based on measured values obtained from each of the plurality of sensors.

The objects described above are also achieved by the method for measuring at least one atmospheric gas in an upper-air region, wherein at least one atmospheric gas is ozone.

According to the above method, since sensors may be made small in size and are able to be placed in a radio sonde, a large measuring system is not necessary. Also, since measurements may be conducted under substantially no influence of unnecessary infrared radiation and water vapor, it is possible to carry out an accurate estimation of the amount of atmospheric gases such as ozone, carbonic acid gas and water vapor based on the measured values by the sensors. Moreover, since a predetermined number of sensors may be placed in a conventional sonde, it is possible to observe atmospheric gases in an upper-air region for 24 hours a day, and hence the accuracy of the measurement may be improved.

The objects described above are also achieved by the method for measuring at least one atmospheric gas in an upper-air region, wherein at least one of the plurality of sensors is coated with a first member so as to eliminate the effect of sun light, and with a second member so as to eliminate the effect of infrared radiation in the atmosphere.

According to the above method, since at least one of the plurality of sensors is-coated with a first member which may eliminate the effect of sun light, and with a second member which may eliminate the effect of infrared radiation in the atmosphere, the effect of sun light and infrared radiation on temperature may be eliminated.

The objects described above are also achieved by the method for measuring at least one atmospheric gas in an upper-air region, wherein the first member is a white paint composition and the second member is gold.

According to the above method, since the first member is a white paint composition and the second member is gold, sun light is reflected by the white paint composition, and no significant errors are caused by a temperature increase due to sun light. Also, infrared radiation of all wavelengths is reflected by the surface of gold deposition and thus a sensor may be kept away from the influence of infrared radiations. Moreover, since gold is not corrosive like other metals, there is no danger that corroded portions may become sensitive to infrared radiation. Thus, it is possible to measure an accurate temperature of each air layer without being affected by sun light and infrared radiation.

The objects described above are also achieved by the method for measuring at least one atmospheric gas in an upper-air region, wherein a surface of at least one of the plurality of sensors is processed to have a sensitivity to infrared radiation from infrared radiative gases, and is further coated with a water repellent agent.

According to the above method, since the surface of at least one of the plurality of sensors is processed to have a sensitivity to infrared radiation from infrared radiative gases, and is further coated with a water repellent agent, a sensor suitable for objective gas(es) which is not affected by water vapor or cloud particles contained in the atmosphere may be obtained.

The objects described above are also achieved by the method for measuring at least one atmospheric gas in an upper-air region, wherein at least one of the plurality of sensors is an ozone/carbonic acid gas sensor for measuring mainly ozone and carbonic acid gas in the air, an upper surface of the sensor being further coated with a SiO layer which is covered by a water repellent layer.

According to the above method, since at least one of the plurality of sensors is an ozone/carbonic acid gas sensor for measuring mainly ozone and carbonic acid gas in the air, an upper surface of which being further coated with a SiO layer which is covered by a water repellent layer, accurate measurement values for ozone and carbonic acid gas present in the atmosphere may be obtained.

The objects described above are also achieved by the method for measuring at least one atmospheric gas in an upper-air region, wherein at least one of the plurality of sensors is a carbonic acid gas sensor for measuring mainly carbonic acid gas in the air, the sensor is coated with a first member which may eliminate the effect of sun light, the lower half of the first member being covered by a second member so as to eliminate an effect of infrared radiation and an upper half of the first member being covered by a water repellent agent.

According to the above method, since at least one of the plurality of sensors is a carbonic acid gas sensor for measuring mainly carbonic acid gas in the air, the sensor is coated with a first member which may eliminate the effect of sun light, the lower half of the first member being covered by a second member which may eliminate the effect of infrared radiation and the upper half of the first member being covered by a water repellent agent, accurate measurement values for carbonic acid gas present in the atmosphere may be obtained.

The objects described above are achieved by a system for measuring at least one atmospheric gas in an upper-air region using a plurality of sensors comprising: a sensor which measures air temperature and is unaffected by gases contained in the air, sensors, each of which measures air temperature and is affected by at least one atmospheric gas contained in the air, and a calculation means which calculates an amount of at least one atmospheric gas based on measured values obtained from each of the plurality of sensors.

The objects described above are also achieved by a recording medium storing a program for causing a computer to perform a process for measuring at least one atmospheric gas in an upper-air region using a plurality of sensors comprising: a computer-readable recording medium for reading a program code; and program code means for calculating an amount of the at least one atmospheric gas based on measured values obtained from each of the plurality of sensors.

According to the above system for measuring at least one atmospheric gas in an upper-air region, since sensors may be made small in size and are able to be placed in a radio sonde, a large measuring system is not necessary. Also, since measurements may be conducted under substantially no influence of unnecessary infrared radiation and water vapor, it is possible to carry out an accurate estimation of the amount of atmospheric gases such as ozone, carbonic acid gas and water vapor based on values measured by the sensors. Moreover, since a predetermined number of sensors may be placed in a conventional sonde, it is possible to observe atmospheric gases in an upper-air region for 24 hours a day, and hence the accuracy of the measurement may be improved.

The objects described above are also achieved by the system for measuring at least one atmospheric gas in an upper-air region, wherein at least one of the plurality of sensors is coated with a first member so as to eliminate an effect of sun light, and with a second member so as to eliminate the effect of infrared radiation in the atmosphere.

According to the above system for measuring at least one atmospheric gas in an upper-air region, since at least one of the plurality of sensors is coated with a first member which may eliminate the effect of sun light, and with a second member which may eliminate the effect of infrared radiation in the atmosphere, a temperature sensor which is not effected by sun light and is not sensitive to infrared radiation may be realized.

The objects described above are also achieved by the system for measuring at least one atmospheric gas in an upper-air region, wherein the first member is a white paint composition and the second member is gold.

According to the above system for measuring at least one atmospheric gas in an upper-air region, since the first member is a white paint composition and the second member is gold, sun light is reflected by the white paint composition, and no significant errors are caused by a temperature increase due to sun light. Also, infrared radiation of all wavelengths is reflected by the gold deposition surface and a sensor may be kept away from the influence of infrared radiations. Moreover, since gold is not corrosive like other metals, there is no danger that corroded portions may become sensitive to infrared radiation. Thus, it is possible to measure an accurate temperature of each air layer without being affected by sun light and infrared radiation.

The objects described above are also achieved by the system for measuring at least one atmospheric gas in an upper-air region, wherein a surface of at least one of the plurality of sensors is further coated with a material sensitive to ozone.

According to the above system, since at least one of the plurality of sensors is further coated with a material sensitive to ozone, an ozone sensor which is not effected by sun light and is not sensitive to infrared radiation may be attained.

The objects described above are also achieved by the system for measuring at least one atmospheric gas in an upper-air region, wherein at least one of the plurality of sensors is an ozone/carbonic acid gas sensor for measuring mainly ozone and carbonic acid gas in the air, an upper surface of the sensor being further coated with a SiO layer which is covered by a water repellent layer.

According to the above system, since at least one of the plurality of sensors is an ozone/carbonic acid gas sensor for measuring mainly ozone and carbonic acid gas in the air, an upper surface of the sensor being further coated with a SiO layer which is covered by a water repellent layer, an ozone/carbonic acid gas sensor which is not effected by sun light and is not sensitive to infrared radiation may be attained.

The objects described above are also achieved by the system for measuring at least one atmospheric gas in an upper-air region, wherein at least one of the plurality of sensors is a carbonic acid gas sensor for measuring mainly carbonic acid gas in the air.

According to the above system, since at least one of the plurality of sensors is a carbonic acid gas sensor, an amount of carbonic acid gas may be obtained without being effected by sun light or infrared radiation.

The objects described above are also achieved by the system for measuring at least one atmospheric gas in an upper-air region, wherein the carbonic acid gas sensor is coated with a first member so as to eliminate the effect of sun light, the lower half of the first member being covered by a second member which may eliminate the effect of infrared radiation and the upper half of the first member being covered by a water repellent agent.

According to the above system, since the carbonic acid gas sensor is coated with a first member which may eliminate the effect of sun light, the lower half of the first member being covered by a second member which may eliminate the effect of infrared radiation and the upper half of the first member being covered by a water repellent agent, a carbonic acid gas sensor which is not effected by sun light and is not sensitive to infrared radiation may be attained.

The objects described above are also achieved by the system for measuring at least one atmospheric gas in an upper-air region, wherein the sensor which measures a temperature of the air and is not affected by gases contained in the air is an air temperature sensor, and the sensors, each of which measures a temperature of the air and is affected by at least one gas contained in the air, include an ozone/carbonic acid gas sensor and a carbonic acid gas sensor.

The objects described above are also achieved by a recording medium storing a program for causing a computer to perform a process for measuring at least one atmospheric gas in an upper-air region using a plurality of sensors including an air temperature sensor, an ozone/carbonic acid gas sensor and a carbonic acid gas sensor comprising: a computer-readable recording medium for reading a program code; and program code means for calculating an amount of the at least one atmospheric gas based on measured values obtained from each of the plurality of sensors including an air temperature sensor, an ozone/carbonic acid gas sensor and a carbonic acid gas sensor.

The objects described above are also achieved by the system for measuring at least one atmospheric gas in an upper-air region comprising a component ratio calculating means which calculates a component ratio of ozone for each air layer using measured values obtained from the air temperature sensor, the ozone/carbonic acid gas sensor and the carbonic acid gas sensor, and an estimation means which controls the component ratio calculating means so that the component ratio calculating means repeats the calculation until there is no change observed in the amount of ozone, of carbonic acid gas and of water vapor, respectively, for all the air layers and estimates the constant amount of ozone, carbonic acid gas and water vapor.

According to the above system, since the component ratio calculating means which calculates a component ratio of ozone and the estimation means which controls the component ratio calculating means so that the component ratio calculating means repeats the calculation until there is no change observed in the amount of ozone, of carbonic acid gas and of water vapor, respectively, for all the air layers, the amount of each gas may be estimated with high accuracy.

The objects described above are also achieved by the system for measuring at least one atmospheric gas in an upper-air region, wherein the air temperature sensor, the ozone/carbonic acid gas sensor and the carbonic acid gas sensor are provided with a radio sonde in a horizontal state, and the calculation means is located on the ground.

According to the above system, since the sensors and the calculation means are provided separately, the total weight of the devices placed in a radio sonde may be reduced.

The objects described above are also achieved by the system for measuring at least one atmospheric gas in an upper-air region which includes a transmission means for transmitting calculated values calculated by the calculation means to the ground.

According to the above system, since only calculated values may necessary be sent to a ground base, the amount of information sent to the base may be reduced, and the process carried out at the ground base may be simplified.

Other objects and further features of the present invention will be apparent from the following detailed description when read in conjunction with the accompanied drawings.

DESCRIPTION OF THE PREFERRED EMBODIMENTS

In the following, a principle and embodiments of the present invention will be described with reference to the accompanying drawings.

Figure 1:
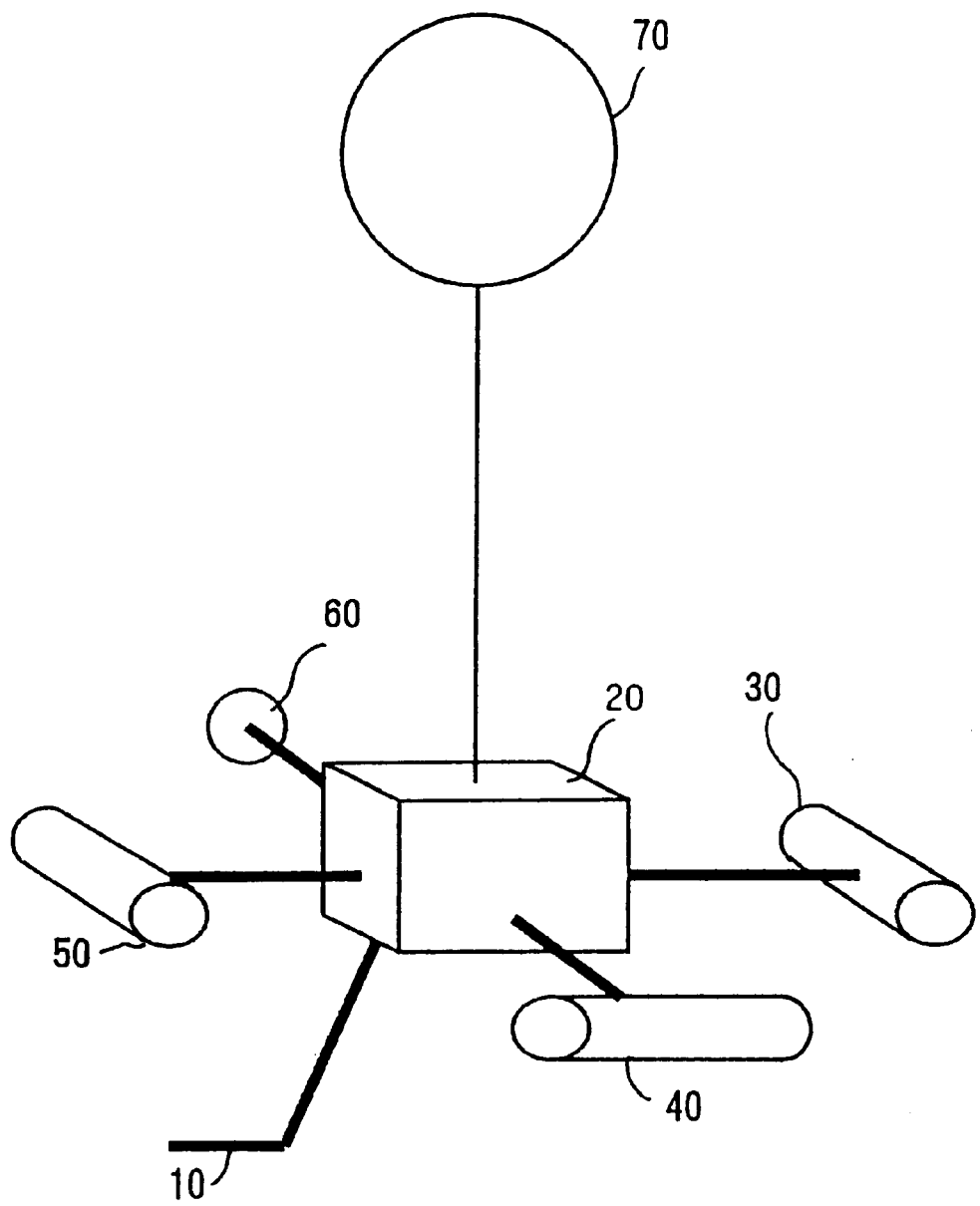
FIG. 1 is a diagram showing a structure of a sensor assembly attached to a sonde according to the present invention.

FIG. 1 is a diagram showing a structure of a sensor assembly attached to a sonde according to the present invention. The sensor assembly shown in FIG. 1 is comprised of an oscillation antenna 10, a measurement control unit 20, an ozone/carbonic gas sensor 30, a carbonic gas sensor 40, an air temperature sensor 50, and an air pressure sensor 60.

The oscillation antenna 10 is used to receive/transmit signals from/to an observation base on the ground. The measurement control unit 20 receives measurement data from each sensor and sends the data to the ground via the oscillation antenna 10. The ozone/carbonic gas sensor 30 measures the ozone and carbonic acid gas content in the air and the carbonic gas sensor 40 measures the carbonic acid gas content in the air only. The air temperature sensor 50 measures a temperature in the air at certain points and the air pressure sensor 60 is used to determine the point at which each of the data is obtained by the respective sensors. Although each of the ozone/carbonic gas sensor 30, the carbonic gas sensor 40, the air temperature sensor 50, and the air pressure sensor 60 is connected to the measurement control unit 20, which is attached to a sonde 70, the structure of the sensor assembly is not limited to the specifically described structure.

Each of the senors 30, 40, 50 and 60 may be coated with a different material which is selected depending on the particular purpose. Examples of such materials include a white paint composition, gold deposition, SiO deposition and water repellents.

The white paint composition, as well known, reflects sun light, and hence a sensor covered by a white paint composition is not effected by sun light.

The gold deposition is not sensitive to infrared radiation, and hence a sensor whose upper surface is coated with the gold deposition becomes insensitive to infrared radiation from above. Likewise, a sensor whose lower surface is coated by gold deposition becomes insensitive to infrared radiation from below. For this reason, infrared radiation from the sun or from the ground due to reflection may be shut out using a gold deposition coating. Note that although the gold deposition is used to make a sensor insensitive to infrared radiation according to the present invention, other materials may be used for the same purpose. At this moment, the gold deposition coating is considered to be the best since problems, such as generation of rust are observed when materials other than gold are used.

The SiO deposition is sensitive only to ozone. Thus, a measurement of ozone becomes possible by deposition of SiO on the surface of a sensor.

The water repellents prevent attachment or freezing of water vapor on the surface of a sensor. Therefore, measurement error due to the attachment or freezing of water vapor may be prevented by using water repellents.

It is possible to construct a sensor which is most effective to measure a certain matter using the above-mentioned materials in accordance with the purpose of the sensor.

Figure 2:
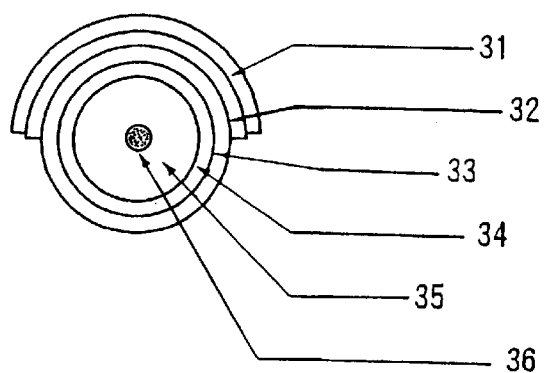
FIG. 2 is a diagram showing an ozone/carbonic acid gas sensor according to an embodiment of the present invention.

FIG. 2 is a diagram showing the ozone/carbonic acid gas sensor 30 according to an embodiment of the present invention. In FIG. 2, the ozone/carbonic gas sensor 30 is comprised of, from an outside to an inside direction, a water repellent layer 31, a SiO deposition layer 32, a gold deposition layer 33, a white paint layer 34, a glass layer 35 and a thermistor 36.

The thermistor 36, which is a measurement member, is located in the center (core) of the sensor 30 and is surrounded by the glass layer 35. Although the gold deposition layer 33 and the white paint layer 34 cover the entire surface of the sensor 30, the water repellent layer 31 and the SiO deposition layer 32 only cover the upper surface of the sensor 30.

According to the ozone/carbonic acid gas sensor 30, water vapor or cloud particles may be prevented from attaching to the sensor 30 by the water repellent layer 31 provided at the outermost surface of the sensor 30, and since the SiO deposition layer 32 is provided, the sensor 30 is capable of measuring the ozone content in the air. Moreover, the gold deposition layer 33 makes the sensor 30 insensitive to infrared radiation. In other words, the sensor 30 is not affected by infrared radiation. Further, the white paint layer 34 eliminates the effect of sun light. Thus, the glass layer 35 may transmit a radiation temperature of only ozone and carbonic acid gas to the thermistor 36 and the data measured by the thermistor 36 are transmitted to the measurement control unit 20.

Figure 3:
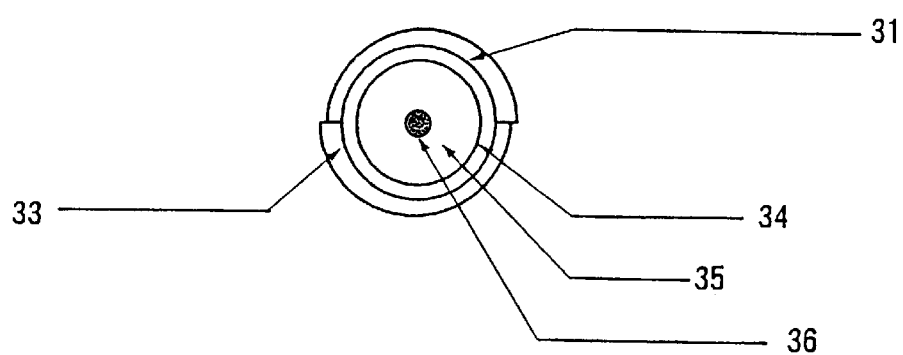
FIG. 3 is a diagram showing a carbonic acid gas sensor according to an embodiment of the present invention.

FIG. 3 is a diagram showing the carbonic acid gas sensor 40 according to an embodiment of the present invention. In FIG. 3, elements which are the same as the ones in FIG. 2 are indicated by the same reference numerals.

The carbonic gas sensor 40 shown in FIG. 3 is comprised of a water repellent layer 31, a gold deposition layer 33, a white paint layer 34, a glass layer 35 and a thermistor 36.

The thermistor 36, which is a measurement member, is located in the center (core) of the sensor 40 and is surrounded by the glass layer 35. Although the white paint layer 34 covers the entire surface of the sensor 40, the water repellent layer 31 covers only the upper surface of the sensor 40 and the gold deposition layer 33 covers only the lower surface of the sensor 40.

According to the carbonic acid gas sensor 40, water vapor or cloud particles may be prevented from attaching to the upper surface of the sensor 40 by the water repellent layer 31, and since the SiO deposition layer 32 is not provided, the sensor 40 has little sensitivity to ozone contained in the air.

Moreover, the gold deposition layer 33 provided with the lower-half of the sensor 40 makes the sensor 40 insensitive to infrared radiation reflected from the ground. Further, the white paint layer 34 eliminates the effect of sun light and the glass layer 35 transmits a radiation temperature of only carbonic acid gas to the thermistor 36. The data measured by the thermistor 36 are transmitted to the measurement control unit 20. Thus, the thermistor 36, which is sensitive to water vapor and clouds as well as carbonic acid gas in nature, may be used for measuring only the carbonic acid gas by using the above-mentioned structure of the sensor 40.

Figure 4:
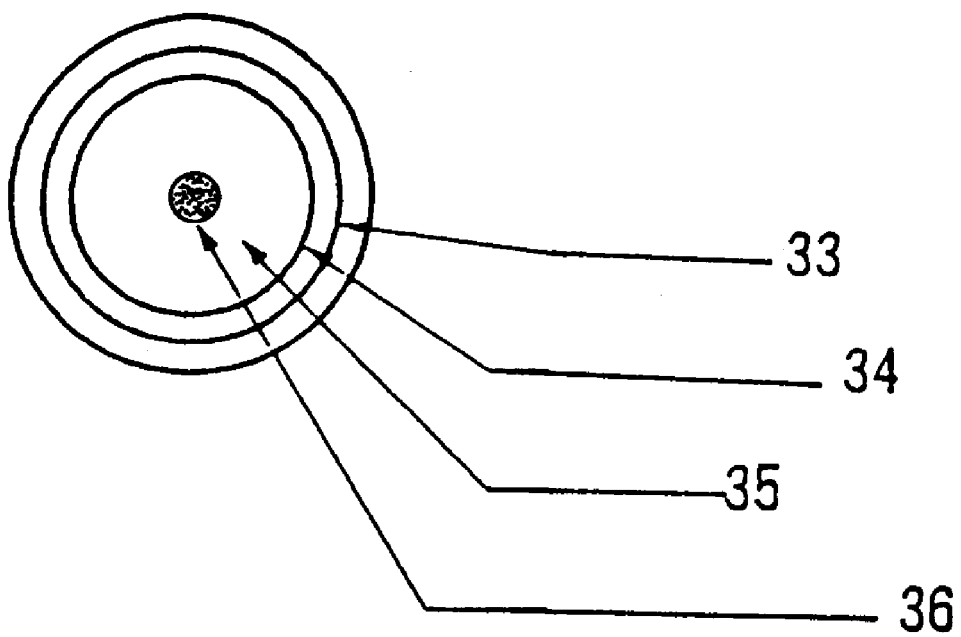
FIG. 4 is a diagram showing an air temperature sensor according to an embodiment of the present invention.

FIG. 4 is a diagram showing the air temperature sensor 50 according to an embodiment of the present invention. In FIG. 4, elements which are the same as the ones in FIG. 2 are indicated by the same reference numerals.

The air temperature sensor 50 shown in FIG. 4 is comprised of a gold deposition layer 33, a white paint layer 34, a glass layer 35 and a thermistor 36.

As shown in FIG. 4, the entire surface of the air temperature sensor 50 is covered by a gold deposition layer 33. Thus, the sensor 50 becomes insensitive to infrared radiation and measurement errors due to the heat generated by infrared radiation will be decreased. Also, the white paint layer 34 eliminates the effect of sun light by reflecting it. Thus, the glass layer 35 may transmit an accurate air temperature to the thermistor 36 and the data measured by the thermistor 36 are transmitted to the measurement control unit 20.

On the other hand, the air pressure sensor 60 (not shown) transmits air pressure parameters to the measurement control unit 20 in order to measure the altitude at which each of the data is obtained by the respective sensors.

In addition, it is preferable that each of the above-mentioned sensors is set substantially horizontal to the sonde 70. This is because some sensors have a structure in which the upper-half and the lower-half are different as mentioned above, and so it is preferable that there is not a large inclination for a position of such sensor.

Next, a method for calculating the gas content in the air using the data transmitted from each of the sensors 20, 30, 40, 50 and 60 will be explained. The calculation is carried out in the measurement control unit 20.

Figure 5:
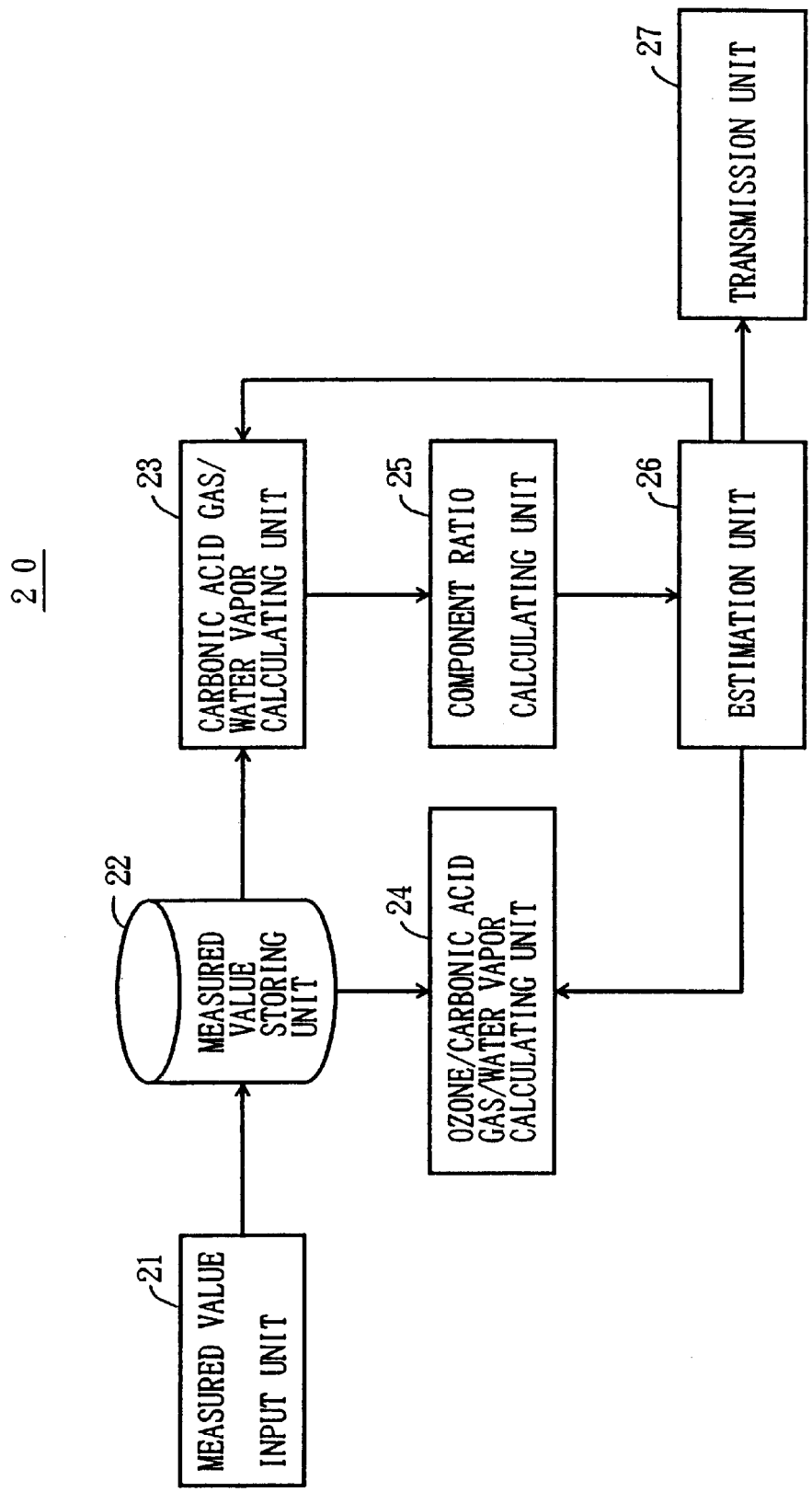
FIG. 5 is a diagram showing a measurement control unit according to an embodiment of the present invention.

FIG. 5 is a diagram showing the measurement control unit 20 according to an embodiment of the present invention. The measurement control unit 20 is comprised of a measured value input unit 21, measured value storing unit 22, a carbonic acid gas/water vapor calculating unit 23, an ozone/carbonic acid gas/water vapor calculating unit 24, a component ratio calculating unit 25, an estimation unit 26 and a transmission unit 27.

Each data taken at various altitudes in the air by the ozone/carbonic gas sensor 30, the carbonic gas sensor 40, the air temperature sensor 50, or the air pressure sensor 60 is input through the measured value input unit 21 and the data are stored in the measured value storing unit 22.

The amounts of carbonic acid gas and water vapor in the troposphere and the stratosphere, respectively, are calculated based on the measured values obtained by the carbonic acid gas sensor 40 and the measured values obtained by the air temperature sensor 50 in the carbonic acid gas/water vapor calculating unit 23.

The amount of ozone, carbonic acid gas and water vapor in the troposphere and the stratosphere, respectively, are calculated based on the measured values obtained by the ozone/carbonic acid gas sensor 40 and the measured values obtained by the air temperature sensor 50 in the ozone/carbonic acid gas/water vapor calculating unit 23.

The ratio of ozone in the air is calculated based on the results obtained from the carbonic acid gas/water vapor calculating unit 23 and the results obtained from the ozone/carbonic acid gas/water vapor calculating unit 24 in the component ratio calculating unit 25.

The estimation unit 26 determines if there is no more change in the value calculated in the component ratio calculating unit 25. If there is a difference between the value obtained and the value previously calculated, the estimation unit 26 orders the ozone/carbonic acid gas/water vapor calculating unit 24 to calculate the value again, and if there is no difference between the current value and the previous value, it transmits the result to the transmission unit 27.

The transmission unit 27 transmits the data obtained from the estimation unit 26 to an observation base on the ground via the oscillation antenna 10.

In addition, the measurement control unit 20 may have a switching function by which each of the sensors is operated in accordance with a certain time so that a desired sensor may be selected for a certain objective gas for a measurement. Also, it is possible to provide a function by which the above-mentioned control of the operation is not carried out and each of the sensors is operated at the same time.

Further, although the measurement control unit 20 is connected to each of the sensors 30, 40, 50 and 60 in FIG. 1, the structure of the measurement control unit 20 is not limited as such, and it is possible, for example, to set the measurement control unit 20 on the ground and receive information from each of the sensors using a transmitting means. In that case, calculation of the amount of a gas may be carried out on the ground.

Figure 6:
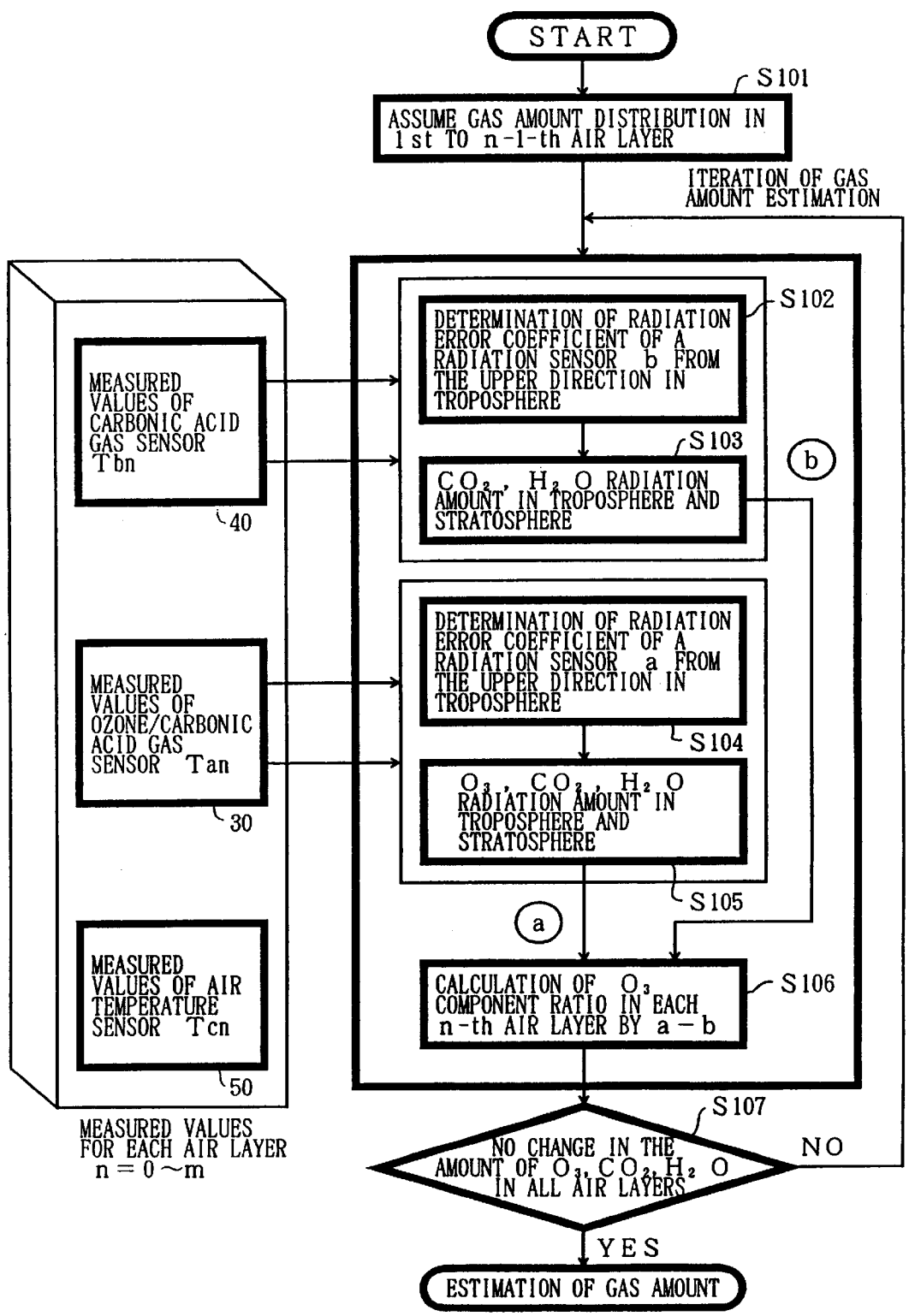
FIG. 6 is a flow chart showing an operation for calculating an amount of an air gas in the measurement control unit according to an embodiment of the present invention.

FIG. 6 is a flow chart showing an operation for calculating an amount of an atmospheric gas at the measurement control unit according to an embodiment of the present invention. Note that in the flow chart shown in FIG. 6, it is assumed that information of the altitude (as indicated by the number of air layers) is already input based on the air pressure value obtained from the air pressure sensor 60. Also, "n" as used in the following explanation indicates an altitude at the n-th air layer.

First of all, the amount of gas distribution in 1st to n-1-th air layer is assumed in step S101. Any known method for carrying out the assumption may be utilized and it is speculated that known distribution of the amount of gas in each air layer is input. These values are initial values for the calculations necessary for obtaining a particular gas ratio in each air layer performed in the following steps S102 to S105.

When a measured value Tbn of carbonic acid gas temperature and a measured value Tcn of an air temperature are input from the carbonic acid gas sensor 40 and the air temperature sensor 50, respectively, the measurement control unit 20 determines a radiation error coefficient (specific heat of a sensor) Cb of the carbonic acid gas sensor 40 from the information obtained at the troposphere.

The radiation error coefficient Cb may be calculated from the following formula:

$$Cb = \text{an average of all the air layers } \{Cbn; n=1, \ldots m\}$$

where $$Cbn = \frac{\sigma\{B''co_2(\theta_e^4 co_2 n + 1 - \theta_e^4 co_2 n) + B''_{H_2O}(\theta_{eH_2O}^4 n + 1 - \theta_{eH_2O}^4 n) - B_b(\theta_b^4 n + 1 - \theta_b^4 n)\}}{(E_{n+1}^{1/2}\delta\theta_{n+1} - E_n^{1/2}\delta\theta_n)}$$

(where σ: Stefan-Boltzmann number,

B''$_{co_2}$: average absorptance of the sensor b in the $CO_2$ absorption band, B''$_{H_2O}$: average absorptance of the sensor b in the $H_2O$ absorption band, Bb: average absorptance of the sensor b in the entire infrared region, $e^4_e co_2 n$: radiant quantity from $CO_2$ gas molecules incident from the upper surface of sensor located in n-th layer, $\theta^4_{eH_2O} n$: radiant quantity from $H_2O$ gas molecules incident from the upper surface of sensor located in n-th layer, $\theta^4_b n$: radiant quantity from all gas molecules incident from the upper surface of sensor located in n-th layer, $$En = V_n \cdot P_n / T_n d,$$

where
$V_n$: ascending velocity of sonde in n-th layer,
$P_n$: air pressure in n-th layer,
$T_n$: air temperature in n-th layer,
d: representative length of sensor, $\delta\theta_n$: radiation error of sensor located in n-th layer=$\sigma(T_{bn}-T_n)$, where
$T_{bn}$: temperature of the sensor b).

Then, the radiation amount of carbonic acid gas and that of water vapor in the troposphere and the stratosphere are calculated using the measured value Tbn obtained from the carbonic acid gas sensor 40 in step S103.

The amount of radiation is used to obtain an amount of infrared radiation which is emitted from the molecules of carbonic acid gas which reach the carbonic acid gas sensor 40, and it is calculated as follows:

$$\Phi_k \times \zeta_{kn}$$

(where $\Phi_k$ indicates a radiation amount from the k-th air layer and is a function for a molecular component ratio, air pressure and temperature. $\zeta_{kn}$ indicates a transmittance from the k-th air layer to an n-th air layer, where the carbonic acid gas sensor 40 is present, and is a function for a molecular component ratio and air pressure.)

When a measured value Tan is input from the ozone/carbonic acid gas sensor 30, the measurement control unit 20 determines a radiation error coefficient Ca of the ozone/carbonic acid gas sensor 30 for the information obtained at the troposphere in step S104.

The radiation error coefficient Ca may be calculated by the following equation:

$$Ca = \text{an average of all the air layers } \{Can; n=1, \ldots m\}$$

where $$Can = \frac{\sigma\{B'O_3(\theta_e^4 O_3 n + 1 - \theta_e^4 O_3 n) + B'co_2(\theta_e^4 co_2 n + 1 - \theta_e^4 co_2 n) + B'_{H_2O}(\theta_{eH_2O}^4 n + 1 - \theta_{eH_2O}^4 n) - B_a(\theta_a^4 n + 1 - \theta_a^4 n)\}}{E_{n+1}^{1/2} \delta\theta_{n+1} - E_n^{1/2} \delta\theta_n}$$

(where σ: Stefan-Boltzmann number,

B'o$_3$: average absorptance of the sensor a in the O$_3$ absorption band,

B'co$_2$: average absorptance of the sensor a in the CO$_2$ absorption band,

B'$_{H2O}$: average absorptance of the sensor a in the H$_2$O absorption band,

Ba: average absorptance of the sensor a in the entire infrared region, $\theta^4_{eO_3}n$: radiant quantity from O$_3$ gas molecules incident from the upper surface of sensor located in n-th layer, $\theta_{4e}co_2n$: radiant quantity from CO$_2$ gas molecules incident from the upper surface of sensor located in n-th layer, $\theta^4_{eH_2O}n$: radiant quantity from H$_2$O gas molecules incident from the upper surface of sensor located in n-th layer, $\theta^4_a n$: radiant quantity from all gas molecules a incident from the upper surface of sensor located in n-th layer, $$E_n = V_n \cdot P_n / T_n d,$$

where $V_n$: ascending velocity of sonde in n-th layer,
$P_n$: air pressure in n-th layer,
$T_n$: air temperature in n-th layer,
d: representative length of sensor, $$\delta\theta_n: \text{ radiation error of sensor located in n-th layer}=\sigma(T_{an}-T_n),$$

where $T_{an}$: temperature of the sensor a).

Next, the measurement control unit 20 calculates the radiation amount of ozone, carbonic acid gas and water vapor using the following formula in step S105:

$$\Phi_k \times \zeta_{kn}$$

(where $\Phi_k$ indicates a radiation amount from the k-th air layer and is a function for a molecular component ratio, air pressure and a temperature. $\zeta_{kn}$ indicates a transmittance from the k-th air layer to an n-th air layer, where the ozone/carbonic acid gas sensor 30 is present, and is a function for a molecular component ratio and air pressure.)

After that, in step S106, the component ratio of ozone at each air layer is calculated using the values obtained in the above steps S103 and S105.

Then, the calculations in the above mentioned step S102 to S106 are repeated for all of the air layers until there is no change in the amount of ozone, carbonic acid gas and water vapor. When there is no change in the amount of ozone, carbonic acid gas and water vapor, the calculation process is terminated.

AS mentioned above, according to the present invention, since sun light is reflected by the white paint composition, no significant errors are caused by a temperature rise due to sun light. Also, infrared radiation of all wavelengths is reflected by the gold deposition surface and thus a sensor may be kept away from the influence of infrared radiation. Moreover, since gold is not corrosive like other metals, there is no danger that corroded portions may become sensitive to infrared radiation. Thus, a white painted sensor which is coated with a gold deposition is not affected by sun light or infrared radiation, it is considered to be an ideal sensor for measuring atmospheric gases. This is confirmed by tests using a radio sonde.

It is necessary to process the surface of a sensor so that the sensor has at least 20% absorption in the absorption band region of an atmospheric gas. For this reason, according to the present invention, a suitable white paint composition is selected for the carbonic acid sensor, and the thickness of SiO deposition is increased for the ozone/carbonic acid gas sensor so that a sensor having 50% absorption capacity may be obtained.

Further, a proper water repellent may be used in order to avoid interference by water vapor or cloud particles which may attached to the surface of a sensor.

Although the above embodiments are explained for only a typical method for measuring atmospheric gases and a typical system for measuring atmospheric gases, it is possible to apply the present invention to any other suitable form of methods and systems for measuring atmospheric gases.

In addition, the present invention is not limited to the above embodiments, and variations and modifications may be made without departing from the scope of the present invention.

What is claimed is:

1. A method for measuring at least one atmospheric gas in an upper-air region using a plurality of sensors comprising:

measuring a temperature of the air using one of said plurality of sensors, which is unaffected by gases contained in the air;

measuring a temperature of the air using some of said plurality of sensors, each of said some of said plurality of sensors being affected by at least one gas contained in the air; and calculating an amount of said at least one atmospheric gas based on measured values obtained from each of said plurality of sensors, wherein at least one of said plurality of sensors is coated with a first member so as to eliminate an effect of sun light, and with a second member so as to eliminate an effect of infrared radiation in the atmosphere.

2. The method for measuring at least one atmospheric gas in an upper-air region as claimed in claim 1, wherein a surface of said at least one of said plurality of sensors is processed to have a sensitivity to infrared radiation from infrared radiative gases, and is further coated with a water repellent agent.

3. The method for measuring at least one atmospheric gas in an upper-air region as claimed in claim 1,
wherein said at least one of said plurality of sensors is an ozone/carbonic acid gas sensor for measuring mainly ozone and carbonic acid gas in the air, an upper surface of said ozone/carbonic acid gas sensor being further coated with a SiO layer which is covered by a water repellent layer.

4. The method for measuring at least one atmospheric gas in an upper-air region as claimed in claim 1, wherein said at least one atmospheric gas is ozone.

5. A system for measuring at least one atmospheric gas in an upper-air region using a plurality of sensors comprising:
a sensor which measures air temperature and is unaffected by gases contained in the air;
other sensors, each of which measures air temperature and is affected by at least one atmospheric gas contained in the air; and
calculation means which calculates an amount of said at least one atmospheric gas based on measured values obtained from each of said plurality of sensors,
wherein at least one of said plurality of sensors is coated with a first member so as to eliminate an effect of sun light, and with a second member so as to eliminate an effect of infrared radiation in the atmosphere.

6. The system for measuring at least one atmospheric gas in an upper-air region as claimed in claim 5, wherein said first member is a white paint composition and said second member is gold.

7. The system for measuring at least one atmospheric gas in an upper-air region as claimed in claim 5, wherein a surface of said at least one of said plurality of sensors is further coated with a material sensitive to ozone.

8. The system for measuring at least one atmospheric gas in an upper-air region as claimed in claim 7,
wherein said at least one of said plurality of sensors is an ozone/carbonic acid gas sensor for measuring mainly ozone and carbonic acid gas in the air, an upper surface of said ozone/carbonic acid gas sensor being further coated with a SiO layer which is covered by a water repellent layer.

9. A system for measuring at least one atmospheric gas in an upper-air region using a plurality of sensors comprising:
a sensor which measures air temperature and is unaffected by gases contained in the air;
other sensors, each of which measures air temperature and is affected by at least one atmospheric gas contained in the air; and
calculation means which calculates an amount of said at least one atmospheric gas based on measured values obtained from each of said plurality of sensors,
wherein said sensor which measures a temperature of the air and is unaffected by gases contained in the air is an air temperature sensor, and said other sensors, each of which measures a temperature of the air and is affected by at least one gas contained in the air, include an ozone/carbonic acid gas sensor and a carbonic acid gas sensor, and are coated so as to eliminate an effect of sun light and an effect of infrared radiation.

10. The system for measuring at least one atmospheric gas in an upper-air region as claimed in claim 9, further comprising a transmission means for transmitting calculated values calculated by said calculation means to the ground.

11. The system for measuring at least one atmospheric gas in an upper-air region as claimed in claim 9, further comprising:
a component ratio calculating means which calculates a component ratio of ozone for each air layer using measured values obtained from said air temperature sensor, said ozone/carbonic acid gas sensor and said carbonic acid gas sensor, and
an estimation means which controls said component ratio calculating means so that said component ratio calculating means repeats calculation, until no change is observed in an amount of ozone, of carbonic acid gas and of water vapor, respectively, for all air layers and estimates a constant amount of ozone, carbonic acid gas and water vapor.

12. The system for measuring at least one atmospheric gas in an upper-air region as claimed in claim 11,
wherein said air temperature sensor, said ozone/carbonic acid gas sensor and said carbonic acid gas sensor are positioned in a horizontal state on a radio sonde, and said calculation means is located at ground level.

13. The method for measuring at least one atmospheric gas in an upper-air region as claimed in claim 1, wherein said first member is a white paint composition and said second member is gold.

14. A method for measuring at least one atmospheric gas in an upper-air region using a plurality of sensors, comprising:
measuring a temperature of the air using one of said plurality of sensors, which is unaffected by gases contained in the air;
measuring a temperature of the air using some of said plurality of sensors, each of said some of said plurality of sensors being affected by at least one gas contained in the air; and
calculating an amount of said at least one atmospheric gas based on measured values obtained from each of said plurality of sensors,
wherein
at least one of said plurality of sensors is a carbonic acid gas sensor for measuring mainly carbonic acid gas in the air, said carbonic acid gas sensor being coated with a first member so as to eliminate an effect of sun light, a lower half of said first member being covered by a second member so as to eliminate an effect of infrared radiation and an upper half of said first member being covered by a water repellent agent.

15. system for measuring at least one atmospheric gas in an upper-air region using a plurality of sensors comprising:
a sensor which measures air temperature and is unaffected by gases contained in the air;
other sensors, each of which measures air temperature and is affected by at least one atmospheric gas contained in the air; and
calculation means which calculates an amount of said at least one atmospheric gas based on measured values obtained from each of said plurality of sensors,
wherein at least one of said plurality of sensors is a carbonic acid gas sensor for measuring mainly carbonic acid gas in the air and is coated so as to eliminate an effect of sun light and an effect of infrared radiation.

16. A system for measuring at least one atmospheric gas in an upper-air region using a plurality of sensors comprising:

a sensor which measures air temperature and is unaffected by gases contained in the air;

other sensors, each of which measures air temperature and is affected by at least one atmospheric gas contained in the air; and calculation means which calculates an amount of said at least one atmospheric gas based on measured values obtained from each of said plurality of sensors, wherein at least one of said plurality of sensors is a carbonic acid gas sensor for measuring mainly carbonic acid gas in the air and the carbonic acid gas sensor is coated with a first member so as to eliminate an effect of sun light, a lower half of said first member being covered by a second member so as to eliminate an effect of infrared radiation and an upper half of said first member being covered by a water repellent agent.

17. A method for measuring at least one atmospheric gas, comprising:

measuring a first air temperature irrespective of an effect of gases contained in the air;

measuring a second air temperature considering an effect of at least one gas one gas contained in the air; and calculating an amount of said at least one gas based on measured values obtained from measuring the first air temperature and the second air temperature, wherein at least one of the air temperature measurements is taken irrespective of an effect of sun light or an effect of infrared radiation.

18. An apparatus measuring at least one atmospheric gas in an upper-air region using a plurality of sensors, comprising:

a plurality of sensors, wherein at least one of said plurality of sensors, which is unaffected by gases contained in the air, measures a temperature of the air and some of the plurality of sensors, which are affected by at least one gas contained in the air, measure a temperature of the air; and a calculation device calculating an amount of said at least one gas based on measured values obtained from each of said plurality of sensors, wherein at least one of said plurality of sensors is coated so as to eliminate an effect of sun light and an effect of infrared radiation.

\* \* \* \* \*